United States Patent [19]
Lavastre et al.

[11] Patent Number: 5,231,092
[45] Date of Patent: Jul. 27, 1993

[54] HEXAHYDROAZEPINE DERIVATIVES AND PHARMACEUTICAL COMPOSITIONS CONTAINING THEM

[75] Inventors: Serge Lavastre, Montpellier; Jean-Pierre Maignan, Portet/Garonne; Raymond Paul, St Gely du Fesc; Martine Poncelet, St Mathieu de Treviers; Vincent Santucci, Combaillaux, all of France

[73] Assignee: Sanofi, Paris, France

[21] Appl. No.: 714,832

[22] Filed: Jun. 13, 1991

[30] Foreign Application Priority Data

Jun. 14, 1990 [FR] France ................................. 90 7434

[51] Int. Cl.$^5$ ..................... A61K 31/55; C07D 223/04
[52] U.S. Cl. ..................................... 514/212; 540/612; 540/484
[58] Field of Search ............... 540/609, 610, 612, 484; 514/212

[56] References Cited

U.S. PATENT DOCUMENTS

| | | | |
|---|---|---|---|
| 2,881,165 | 4/1959 | Janssen et al. | 260/234 |
| 4,104,383 | 8/1978 | Krausz | 514/212 |
| 4,465,678 | 8/1984 | Knops et al. | 424/244 |

FOREIGN PATENT DOCUMENTS

| | | |
|---|---|---|
| 54424/86 | 9/1986 | Australia. |
| 0163537 | 12/1985 | European Pat. Off.. |
| 1545561 | 12/1969 | Fed. Rep. of Germany. |

OTHER PUBLICATIONS

Proceedings of the National Academy of Sciences of the United States of America, Aug. 1984, vol. 81, No. 15, pp. 4983-4987.
Organic Chemistry, Third Edition, James B. Hendrickson et al., pp. 585-586.
Catalytic Hydrogenation, Robert L. Augustine, 1965, M. Dekker, Inc., New York.

*Primary Examiner*—John M. Ford
*Attorney, Agent, or Firm*—Bacon & Thomas

[57] ABSTRACT

The present invention relates to hexahydroazepine derivatives of formula

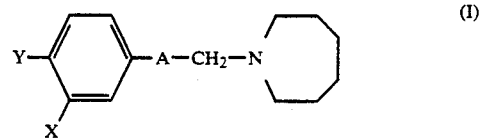

in which:
A=—CO—CH$_2$—, —CH(OH—CH$_2$—; —CH$_2$—CH$_2$—CH$_2$—;—CH=CH—; —C≡C—;
X=H or a halogen;
Y=cylcohexyl or, when X is H, phenyl.

It likewise relates to the salts of the said derivatives, to a process for the preparation of these and to the pharmaceutical compositions containing them, more particularly as antipsychotic agents.

14 Claims, No Drawings

HEXAHYDROAZEPINE DERIVATIVES AND PHARMACEUTICAL COMPOSITIONS CONTAINING THEM

The present invention relates to hexahydroazepine derivatives binding specifically to sigma receptors, especially to those of the central nervous system, to a process for the preparation of these compounds and to pharmaceutical compositions containing them, more particularly as antipsychotic agents.

Sigma receptors have been demonstrated with the aid of several ligands. First of all, an opiate compound, N-allylnormetazocine or SKF-10047, more particularly the chiral compound (+) SKF-10047, can be cited (W. R. Martin et al., J. Pharmacol. Exp. Ther., 1976, 197, 517–532; B. R. Martin et al., J. Pharmacol. Exp. Ther., 1984, 231, 539–544). A neuroleptic agent, haloperidol, is likewise a sigma receptor ligand, as well as (+) 3-(3-hydroxyphenyl)-1-propyl piperidine or (+) 3-PPP (B. L. Largent et al., Proc, Nat. Acad. Sci. U.S.A., 1984, 81, 4983–4987).

The U.S. Pat. No. 4,709,094 described guanidine derivatives which are very active as specific sigma receptor ligands.

The anatomical distribution of sigma receptors in the brain has been studied by autoradiography, after labelling of these receptors by one of the ligands described in the above U.S. patent, namely di-o-tolylguanidine, according to E. Weber et al., Proc. Natl. Acad. Sci. U.S.A., 1986, 83, 8784–8788, as well as by the ligands (+) SKF-10047 and (+) 3-PPP according to B. L. Largent et al., J. Pharmacol, Exp. Ther., 1986, 238, 739–748. The autoradiographic study allowed the sigma receptors of the brain to be clearly identified and to be distinguished from other opiate receptors, such as those of phencyclidine.

The Patent FR 2 249 659 describes compounds of formula:

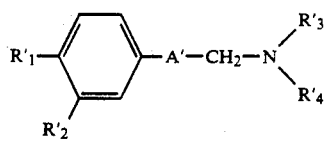

in which:
A' represents the —$CH_2$—$CH_2$— group or the —CH=CH— group;
R'$_1$ represents the cyclohexyl group or the phenyl group;
R'$_2$ represents hydrogen or a halogen;
R'$_3$ represents hydrogen or a $C_1$—$C_3$-alkyl group;
R'$_4$ represents a $C_1$—$C_3$alkyl group; or R'$_3$ and R'$_4$, taken together with the nitrogen atom to which they are bonded, can form a heterocyclic group.

All the specific products described in the document above are of trans configuration when A=—CH=CH— and are described as having an antidepressive activity.

The Patent EP 040 744 describes compounds of formula:

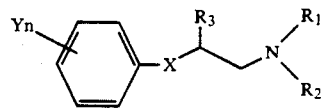

in which
R$_1$ and R$_2$ represents an alkyl group or, together with the nitrogen atom to which they are bonded, form a heterocycle;
R$_3$ is hydrogen or an alkyl group;
X is an keto group or an oxime of formula >C=N—OR$_4$;
Y is an alkyl group, a halogen, a haloalkyl group, an alkoxy group, an alkylthio group, a cycloalkyl group, a haloalkylthio group or a cyano group;
n is 0, 1, 2 or 3.

For these compounds of formula (B), a fungicidal activity is described.

A novel series of hexahydroazepine derivatives having no anti-depressive activity and having unexpected and surprising antipsychotic properties, binding selectively to sigma receptors and devoid of affinity for dopaminergic receptors has now been found.

Thus, the present invention relates to novel N-substituted hexahydroazepines of formula:

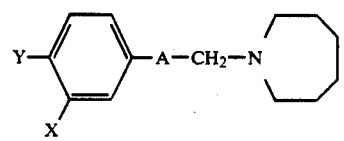

in which:
A is a group chosen from amongst the following: —CO—$CH_2$—, —CH(OH)—$CH_2$—; —CH$_2$—$CH_2$—; —CH=CH—; —C≡C—;
X represents hydrogen or a halogen;
Y is a cyclohexyl group or, when X is hydrogen, a phenyl group;
as well as their salts with mineral or organic acids.

According to the invention, halogen atom is understood to mean fluorine, chlorine, bromine or iodine atoms, the chlorine atom being preferred.

When A represents a vinylene grouping, the compounds (I) of cis and trans configuration are an integral part of the invention.

When A represents a hydroxyethylene grouping, the compounds (I) of cis and trans configuration are an integral part of the invention.

When A represents a hydroxyethylene grouping, the compounds (I) have an asymmetric carbon atom. The racemates as well as the optically active isomers of these compounds are an integral part of the invention.

The salts of the compounds of formula (I) according to the present invention also include those with mineral or organic acids which allow an expedient separation or a crystallisation of the compounds of formula (I), such as picric acid, oxalic acid or an optically active acid, for example a mandelic acid or a camphorsulphonic acid, and those which form pharmaceutically acceptable salts such as the hydrochloride, the hydrobromide, the sulphate, the hydrogensulphate, the dihydrogenphosphate, the methanesulphonate, the acetate, the benzoate, the citrate, the glutamate, the methylsulphate, the maleate, the fumarate and the 2-naphthalenesulphonate.

The compounds of formula (I) in which Y is a cyclohexyl group are preferred.

The hydrochloride of cis-3-(hexahydroazepin-1-yl)-1-(3-chloro-4-cyclohexylphenyl)-1-propene is particularly preferred.

The present invention likewise relates to a process for the preparation of the compounds (I), characterised in that:

a) a condensation reaction is carried out with formaldehyde and hexahydroazepine,
either on the acetophenone of formula:

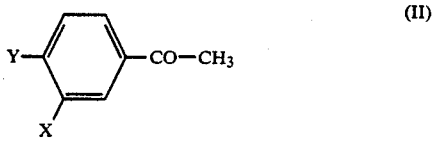

in which X and Y have the meanings indicated above for (I), to obtain a compound (I) according to the invention in which A represents the —CO—CH$_2$— grouping,
or on a phenylacetylene derivative of formula:

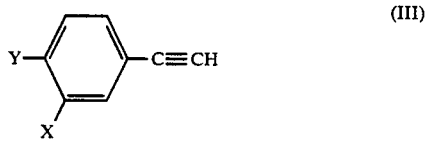

in which X and Y have the meanings indicated above for (I), to obtain a compound (I) according to the invention in which A represents the —C≡C— grouping;

b) if appropriate, a reducing agent is reacted with the compound (I) in which A represents a —CO—CH$_2$— grouping to prepare the compound (I) according to the invention in which A represents a —CHOH—CH$_2$— grouping;

c) if appropriate, a hydrogenation by nascent hydrogen of the compound (I) in which A represents the acetylenic grouping —C≡C— is carried out to prepare the compound (I) in which A represents the —CH=CH— group in the form of a mixture of cis and trans isomers, or a hydrogenation is carried out in the presence of a supported metal catalyst to prepare the vinylene compound (I) in cis form, or alternatively the compound (I) in which A represents a —CHOH—CH$_2$— grouping is dehydrated to prepare the vinylene compound (I) in trans form;

d) if appropriate, a hydrogenation of the compound (I) in which A represents a —CH=CH— grouping or a —C≡C— grouping is carried out to prepare the compound (I) according to the invention in which A represents the —CH$_2$—CH$_2$— grouping;

e) finally, if necessary, an acid addition salt of a compound (I) is prepared by addition of an appropriate mineral or organic acid.

The starting acetophenones (II) are known ore are prepared according to known methods such as those described in Gazz Chim. Ital. 1949, Volume 79, 453–457 and J. Am. Chem. Soc. 1947, Volume 69, 1651-1652.

When the condensation of step a) of the process according to the invention is carried out on the acetophenone (II) by preparing a chlorophenylethylene derivative of formula

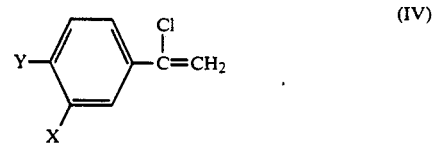

by the action of phosphorus pentachloride on the acetophenone (II) and hydrolysis and then by carrying out a dehydrohalogenation of the compound (IV) in basic medium.

Staring form the acetophenone (II), it is likewise possible to prepare an intermediate semi-carbazone (V) and then to apply the method of operation described by I. LALEZARI et al. (Angew. Chem., Internat. Ed., 1970, 9 (6) 464) by reacting selenium dioxide, in the presence of heat, in acidic medium, then by decomposing the resulting intermediate selenodiazole (VI) in the presence of heat and thus to obtain the phenylacetylene derivative (III) according to the following reactions scheme:

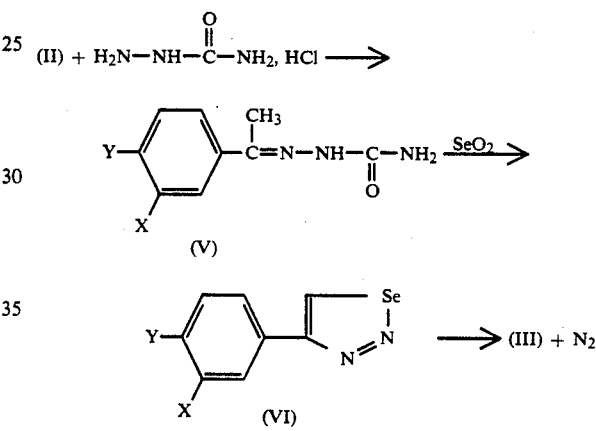

When step a) of the process according to the invention is carried out on the phenylacetylene derivative (III), the process is carried out in the presence of heat, in an inert solvent such as dioxane or dimethoxyethane; to facilitate the condensation reaction, a metallic salt such as cuprous chloride or cupric chloride can be used as a catalyst.

In step b) of the process, the reducing agent is preferably a metallic hydride such as, for example, sodium borohydride, and the reaction is preferentially carried out in an alcoholic solvent at a temperature below 10° C.

In step c) of the process: 1) the hydrogenation by nascent hydrogen can be carried out by the action of zinc in acetic acid; or 2) when the hydrogenation is carried out in the presence of a supported metal catalyst such as a palladium on barium sulphate or on calcium carbonate, or Raney nickel, in an alcoholic solvent or a solvent containing a proportion of alcohol, the reaction can be carried out in the presence of quinoline to facilitate the reaction; the catalytic hydrogenation realised int his way leads uniquely to compounds (I) of cis configuration (Catalytic Hydrogenation—R. L. Augustine—New York: Marcel Kekker, 1965, p69-71); or 3the dehydrating agent for the compound (I) in which A represents a —CHOH—CH$_2$— grouping is, for example, p-toluenesulphonic acid which is used in toluene, at the reflux temperature of ht reaction mixture.

In step d) of the process, the reaction can be carried out in the presence of a catalyst, for example platinum oxide.

The product of formula (I) is isolated, in the form of the free base or the salt, according to the conventional techniques.

When the compound of formula (I) is obtained in the form of the free base, salt formation is carried out by treatment with the chosen acid in an organic solvent. By treating the free base, dissolved, for example, in an alcohol such as isopropanol, with a solution of the chosen acid in the same solvent the corresponding salt is obtained which is isolated according to the conventional techniques. Thus, for example, the hydrochloride, the hydrobromide, the sulphate, the hydrogensulphate, the dihydrogenphosphate, the methanesulphonate, the methylsulphate, the oxalate, the maleate, the fumarate or the 2-naphthalenesulphonate is prepared.

At the end of the reaction, the compound of formula (I) can be isolated in the form of one of its salts, for example the hydrochloride or the oxalate; in this case, if its is necessary, the free bas can be prepared by neutralising the said salt with a mineral or organic base such as sodium hydroxide or triethylamine or with an alkali metal carbonate or bicarbonate, such as sodium or potassium carbonate or bicarbonate.

In biochemical and pharmacological screening tests, the compounds (I) according to the invention and their salts have shown their capacity to interact with sigma receptors. These test have been carried out in vitro on rate cerebral membranes using as ligands either $^3H-(+)-3$ PPP according to Larent et al., J. Pharmacol. Exp. Ther., 1986, 238, 739–740, or $^3H$-DG according to Weber et al., Proc. Nat. Acad. Sci. U.S.A., 1986, 83, 18784–8788 and in vivo in mice with the ligand $^3H$-3 PPP according to B. Kenneth Koe et al., European J. Pharmacol., 1989, 161, 263–266.

The properties of the invention compounds on the sigma receptors are very surprising because the compounds disclosed in FR patent 2249659 are not active on these receptors or their activity is very moderate.

These same compounds and their salts were shown to be active as antagonists in the predictive test for antipsychotic activity of hyperactivity induced in mice by d-amphetamine according to P. Simon et al., La farmacoterapia nella schizofrenia, 1970, 49–66, Milan, Picioni Mariotti, Pisa Ed.

These compounds do not show, in vitro as well as in vivo, affinity for the dopaminergic receptor(s) in tests carried out according to Fields et al., Brain Research, 1987, 136, 578–584 and Leslie et al., Brain Research, 1987, 253–262.

The compounds according to the invention therefore prove to be, according to these biochemical and behavioral tests, potential antipsychotic agents without direct impact at the dopaminergic level.

A representative compound, the compounds of following Example 2, compared to a known antipsychotic agent, shows the following properties:

TABLE I

| | Binding in vitro | | | |
|---|---|---|---|---|
| | $IC_{50}$ nM DTG | 3-PPP | $IC_{50}$ nM TCP | spiroperidol |
| Compound of Ex. 2 | 10 | 8 | >10,000 | = 10,000 |
| Haloperidol | 43 | 41 | >10,000 | 6 |

$IC_{50}$ = molar concentration necessary to displace 50% of the specifically bound ligand; DTG = di-o-tolylguanidine; 3-PPP = (+) 3-(3-hydroxyphenyl)-1-propylpiperidine; TCP = thienylcyclohexylpiperidine.

From this table, it is evident that compound of Example 2 has a superior and/or more selective sigma impact than that of haloperidol. In vivo, this invention compound provided to be active in mice on the displacement of the ligand (+)−3PPP, at the cerebral level, as well as on the hyperactivity induced by d-amphetamine.

The compounds according to the present invention are therefore useful as medicaments, especially for the treatment of psychotic disorders.

The compounds of the present invention have little toxicity; in particular, their acute toxicity is compatible with their use as a medicament. For such a use, an efficacious quantity of a compound of formula (I) or of one of its pharmaceutically acceptable salts is administered to mammals.

The compounds of the present invention are generally administered in dosage units. The said dosage units are preferably formulated in pharmaceutical compositions in which the active principle is mixed with a pharmaceutical excipient.

Thus, according to another of its aspects, the present invention relates to pharmaceutical compositions containing, as the active principle, a compound of formula (I) or one of its pharmaceutically acceptable salts.

In the pharmaceutical compositions of the present invention for oral, sublingual, subcutaneous, intramuscular, intravenous, transdermal, local or rectal administration, the active ingredients can be administered in unit administration forms, mixed with conventional pharmaceutical carries, to animals and to humans. The appropriate unit administration forms comprise the oral forms such as tablets, capsules, powders, granules and oral solutions or suspensions, sublingual and buccal administration forms, subcutaneous, intramuscular, intravenous, intranasal or intraocular administration forms and rectal administration forms.

When a solid composition is prepared in the form of tablets, the principal active ingredient is mixed with a pharmaceutical vehicle such as gelatin, starch, lactose, magnesium stearate, talc, gum arabic or analogues. The tablets can be coated with sucrose or other appropriate materials or alternatively the can be treated in such a way that they have a sustained or delayed activity and that they liberate a predetermined quantity of active principle in a continuous fashion.

A preparation in capsules is obtained by mixing the active ingredient with a diluent and pouring the mixture obtained into soft or hard capsules.

A preparation in the form of syrup or of elixir may contain the active ingredient together with a sweetening agent, preferably a caloric, methylparaben and propylparaben as antiseptic, as well as a flavour-imparting agent and an appropriate colorant.

The powders or the water-dispersible granules can contain the active ingredient mixed with dispersing agents or wetting agents, or suspending agents, like polyvinylpyrrolidone, as well as with sweeteners or flavour correctants.

For rectal administration, use is made of suppositories which are prepared with binders melting at rectal temperature, for example cocoa butter or polyethylene glycols.

For parenteral, intranasal or intraocular administration, aqueous suspensions, isotonic saline solutions or sterile and injectable solutions are used which contain pharmacologically compatible dispersing agents and/or wetting agents, for example propylene glycol or butylene glycol.

The active principle can likewise be formulated in the form of microcapsules, if appropriate with one or ore carriers or additives.

The compounds of formula (I) above and their pharmaceutically acceptable salts can be used in daily doses of 0.01 to 100 mg per kilo of body weight of the mammal to be treated, preferably in daily doses of 0.1 to 50 mg/kg. In humans, the dose can preferably be varied form 0.5 to 4000 mg per day, more particularly from 2.5 to 1000 mg according to the age of the subject to be treated or the type of treatment: prophylactic or curative. Advantageously, the dosage units contain form 0.5 to 1000 mg of active principle of formula (I).

The following examples illustrate the invention without, however, limiting it.

EXAMPLE 1

1-(Hexahydroazepin-1-yl)-3-(3-chloro-4-cyclohexylphenyl)-3-propyne hydrochloride A) 3-Chloro-4-cyclohexyl-1-ethynylbenzene.

129 g of phosphorus pentachloride are added in small portions, in the course of 30 minutes, to 118.3 g of 3-chloro-4-cyclohexylacetophenone. The mixture is heated to 105° C. in the course of one hour, this temperature is maintained for 1 hour and a half, then the mixture is heated to 115° C. for a further 1 hour and a half. The resulting gum is extracted with ethyl ether, and ethereal phase is washed with 5% NaOH, dried and concentrated. 107 g of 3-chloro-4-cyclohexyl-α-chlorostyrene are obtained. This product is dissolved in 450 ml of ethanol and then heated to reflux for 24 hours in the presence of 94 g of KOH. The greater part of the alcohol is concentrated and replaced by water, and the mixture is extracted with ethyl ether, dried and concentrated to obtain 72. 5 g of crude product. After distillation under reduced pressure, 41.7 g of a liquid are obtained Boiling point: 102°-104° C. at 4 mm of mercury (=533 Pa).

B) 1-(Hexahydroazepin-1-yl)-3-(3-chloro-4-cyclohexylphenyl)-3-propyne hydrochloride A mixture of 9.5 g of he product obtained above according to A) and of 0.18 g of cuprous chloride is stirred at ambient temperature in 40 ml of dimethoxyethane. A mixture of 5.16 g of hexahydroazepine and 6.28 g of 35% aqueous formaldehyde dissolved in 40 ml of dimethoxyethane is then added dropwide to this solution and the reaction mixture is then heated to reflux for 1 hour.

The solvents are concentrated in vacuo, the residue is taken up in a 5% NaOH solution and extracted with either, and the extract is washed with water and with a saturated solution of sodium chloride, dried over $Na_2SO_4$, filtered and concentrated in vacuo. The residue is taken up in 250 ml of ethyl acetate and the addition of ethereal hydrogen chloride allows the preparation of the hydrochloride, which crystallises and is separated by filtration.

m=14.8 g.
m.p.=198° C.

EXAMPLE 2 cis-3-(Hexahydroazepin-1-yl)-1-(3-chloro-4-cyclohexylphenyl)-1-propene hydrochloride 12.8 g of free base of the compound obtained above according to Example 1 are hydrogenated at atmospheric pressure and at ambient temperature in a solution of 100 ml of ethyl acetate and of 5 ml of methanol, in the presence of 0.4 g of 5% Pd on barium sulphate.

The catalyst is separated by filtration, the filtrate is concentrated in vacuo and the residual oil is chromatographed on silica gel, eluting with: dichloromethane/methanol: 98:2 to 95:5. The pure product fractions are concentrated in vacuo, the residue is taken up in 150 ml of ethyl acetate and the addition of ethereal hydrogen chloride allows the preparation of the hydrochloride, which is separated by filtration.

m=8.8 g.
m.p.=168° C.

EXAMPLE 3

1-(Hexahydroazepin-1-yl)-2-(3-chloro-4-cyclohexylbenzoyl)ethane hydrochloride

A mixture of 50 g of 4-cyclohexyl-3-chloroacetophone, 37.7 g of hexahydroazepin hydrochloride, 8.5 g of trioxane and 50 ml of ethanol is heated to reflux for 2 hours in the presence of 0.85 ml of concentrated hydrochloric acid. The mixture solidifies hot.

It is cooled and filtered, an the precipitate is washed with ethanol. The precipitate is recrystallised in a minimum of ethanol. The colourless crystals obtained are washed with ethanol and then dried.

m=42.7 g.
m.p.=208° C.

EXAMPLE 4

1-(Hexahydroazepin-1-yl)-3-(3-chloro-4-cyclohexylphenyl)-3-propanol hydrochloride 20 ml of sodium hydroxide are added to a suspension of 30 g of the compound obtained above according to Example 3 in 250 ml of methanol and the mixture is then cooled to a temperature below +5° C. 7.7 g of sodium borohydride are then added in small portions while maintaining the temperature. The mixture is rendered homogeneous by addition of 100 ml of THF. The temperature is allowed to rise again and the mixture is stirred for 12 hours. 700 mol of cold water are then added nd the mixture is extracted with ether. The organic phase is separated, washed with water until neutral, dried and finally concentrated in vacuo. 26. 9 g of an oil are obtained of which 6.9 g are dissolved in 200 ml of isopropyl ether. A solution of hydrochloric acid in ethanol is added until an acid pH is obtained. The resulting precipitate is separated and then recrystallised in ethanol. 4.8 g of a colourless compound are obtained.
m.p.=198°-200° C.

EXAMPLE 5 trans-3-(Hexahydrazepin-1-yl)-1-(3-chloro-4-cyclohexylphenyl)-1-propene hydrochloride 20 g of base corresponding to the compound obtained above according to Example 4 and 16.3 g of p-toluenesulphonic acid monohydrate are heated to reflux in 500 ml of toluene for 24 hours in an apparatus equipped with a water separator. The mixture is cooled an a mixture of 10 ml of sodium hydroxide in 300 ml of water is added. The organic phase is separated whilst the aqueous phase is extracted with ether. The combined organic phases are washed with water, dried and then concentrated. 18.2 g of an oil are obtained which is taken up in isopropyl ether and acidified with a solution of hydrochloric acid in ethanol. The precipitate hydrochloride is filtered, washed and finally recrystallised in acetonitrile. 10.7 g of a colourless compound are obtained.

m.p.=216° C.

EXAMPLE 6

1-(Hexahydroazepin-1-yl)-3-(3-chloro-4-cyclohexylphenyl propane hydrochloride

A solution of 5 g of the compound obtained above according to Example 5 is hydrogenated under normal pressure in the presence of 250 mg of palladium on carbon (5%). The theoretical volume (304 ml) of hydrogen is absorbed in about ½ hour. The catalyst is then filtered and the solution is concentrated to dryness. The residue recrystallised in acetonitrile yields 3.2 g of a colourless compound.

m.p.=196°-197°C.

We claim:

1. A hexahydroazepine derivative having no anti-depressive activity of formula:

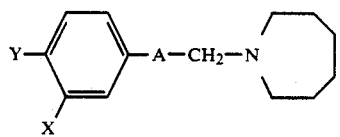

(I)

in which:

A is a —CH=CH—(cis) group;

X represents hydrogen or a halogen;

Y is a cyclohexyl group or, when X is hydrogen, a phenyl group; or their pharmaceutically acceptable addition salts with mineral or organic acids.

2. A compound according to claim 1 of formula (I) in which Y represents a cyclohexyl group.

3. A compound according to claim 1 which has a high sigma selectivity and which has no affinity for dopaminergic receptors.

4. cis-3-(Hexahydroazepin-1-yl)-1-(3-chloro-4-cyclohexylphenyl)-1-propene, or a pharmaceutically acceptable addition salt with a mineral or organic acid.

5. A compound according to claim 4 which is in the form of a hydrochloride.

6. A pharmaceutical composition containing, as active principle, a compound according to claim 1 together with a pharmaceutical excipient.

7. A pharmaceutical composition containing, as active principle, a compound according to claim 2 together with a pharmaceutical excipient.

8. A pharmaceutical composition containing, as active principle, a compound according to claim 4, together with a pharmaceutical excipient.

9. A pharmaceutical composition according to claim 6, in the form of dosage units comprising 0.5 to 1000 mg of active principle.

10. A method of treating psychotic disorders without antidepressive activity in a mammal suffering from psychotic disorders, which method comprises administering to said mammal an effective amount of a compound according to claim 1.

11. A method according to claim 10 wherein the mammal is a human.

12. A method according to claim 11 wherein the effective amount is 0.5 to 4000 mg per day.

13. A method according to claim 12 wherein the effective amount is 2.5 to 1000 mg per day.

14. A method of treating psychotic disorders without anti-depressive activity in a mammal suffering from psychotic disorders, which method comprises administering to said mammal an effective amount of a compound according to claim 3.

* * * * *